United States Patent
Gershenson

(10) Patent No.: US 7,236,201 B1
(45) Date of Patent: Jun. 26, 2007

(54) METHOD OF GENERATING AN IMAGE IN A TURBID MEDIUM

(75) Inventor: Meir Gershenson, Panama City, FL (US)

(73) Assignee: The United States of America as represented by the Secertary of the Navy, Washington, DC (US)

( * ) Notice: Subject to any disclaimer, the term of this patent is extended or adjusted under 35 U.S.C. 154(b) by 735 days.

(21) Appl. No.: 10/779,546

(22) Filed: Feb. 12, 2004

(51) Int. Cl.
  *G03B 17/08* (2006.01)
  *G06K 9/40* (2006.01)
(52) U.S. Cl. .................. 348/370; 348/31; 348/81; 348/371; 348/222.1; 396/28
(58) Field of Classification Search .............. 348/31, 348/81, 122, 50, 124, 370; 356/342; 396/28
See application file for complete search history.

(56) References Cited

U.S. PATENT DOCUMENTS

| | | | | |
|---|---|---|---|---|
| 2,860,306 A | * | 11/1958 | Towner | 324/89 |
| 4,777,501 A | * | 10/1988 | Caimi et al. | 396/28 |
| 5,233,415 A | * | 8/1993 | French et al. | 348/31 |
| 5,532,738 A | * | 7/1996 | Stern | 348/61 |
| 6,088,470 A | * | 7/2000 | Camus et al. | 382/117 |
| 6,348,942 B1 | * | 2/2002 | Watkins | 348/81 |
| 6,459,818 B1 | * | 10/2002 | George | 382/254 |
| 6,512,887 B2 | * | 1/2003 | Inoue et al. | 396/28 |
| 6,724,467 B1 | * | 4/2004 | Billmers et al. | 356/5.04 |

* cited by examiner

*Primary Examiner*—David Ometz
*Assistant Examiner*—Pritham D. Prabhakher
(74) *Attorney, Agent, or Firm*—James T. Shepherd

(57) ABSTRACT

A method is provided for the generation an image in a turbid medium. After illuminating locations along a each of three adjacent lines using beam(s) of light, a camera is activated to generate three separate images. The second line is between the first and third lines. In terms of amplitude associated therewith, a portion of each of the first image and third image are subtracted from the entirety of the second image to generate a resulting image.

20 Claims, 2 Drawing Sheets

METHOD OF GENERATING AN IMAGE IN A TURBID MEDIUM

ORIGIN OF THE INVENTION

The invention described herein was made in the performance of official duties by an employee of the Department of the Navy and may be manufactured, used, licensed by or for the Government for any governmental purpose without payment of any royalties thereon.

1. Field of the Invention

The invention relates generally to the generation of images, and more particularly to a method of generating an image in turbid mediums such as sediment-filled water, smoke and fog.

2. Background of the Invention

The greatly-reduced range of visibility in a turbid medium (e.g., sediment-filled water, smoke-filled air, fog, etc.) makes optical imaging therein a difficult task. For example, the range of visibility in coastal silt-filled water can be reduced to a few centimeters. In such environments, light energy emanating from a self-illuminated target/object is attenuated and scattered before reaching an optical imager (e.g., a camera). In terms of an externally illuminated target/object, backscattering (or glare glow as it is known) forms an illumination source. At the same time, the exponential attenuation of any illumination reflected from the target/object means that the intensity of the glare glow tends to dominate at increased distances from the target/object.

Current methods of generating optical images in a turbid medium are known as time gating and laser scanning. In time gating, an imager is triggered at a time corresponding to direct propagation from the light source to the target and back. While both glare glow and scattered light are reduced, time gating is expensive and the apparatus used is not easily scaled down in size for use on autonomous vehicles. In laser scanning, a laser beam illuminates a target while photo detectors are used to detect reflected light energy. Because the light source and imager are separated, the glare glow of the illumination beam and that associated with reflected light energy will be distinct in space so that image intensity is not masked by the glare glow. However, the image is constructed from individual pixels by cooperatively scanning the illumination laser beam and the imager. Unfortunately, such cooperative scanning involves the use of expensive and unreliable mirror scanners.

SUMMARY OF THE INVENTION

Accordingly, it is an object of the present invention to provide a method of generating an image of a region in a turbid medium.

Another object of the present invention is to provide a method of generating an optical image in a turbid medium using a simple and inexpensive optical imaging system.

Other objects and advantages of the present invention will become more obvious hereinafter in the specification and drawings.

In accordance with the present invention, a method of generating an image of a region in a turbid medium uses a camera focused at a region of a turbid medium. After illuminating a first plurality of locations along a first line in the region using beams of light, the camera is activated to generate a first image. Next, after illuminating a second plurality of locations along a second line in the region using beams of light, the camera is activated to generate a second image. The second line is adjacent to the first line. A third plurality of locations along a third line in the region are then illuminated and the camera is again activated to generate a third image. The third line is adjacent to the second line with the second line being between the first and third lines. In terms of amplitude associated therewith, a portion of each of the first image and third image are subtracted from the entirety of the second image, wherein a resulting image is generated.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
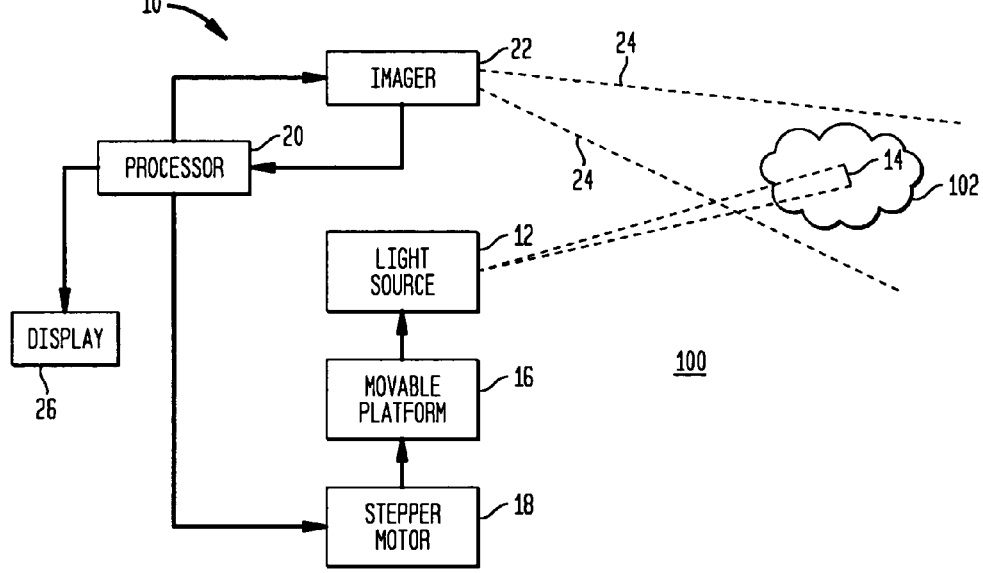
FIG. 1 is a block diagram of an embodiment of a system used to generate an image in a turbid medium in accordance with the present invention.

Referring now to the drawings, and more particularly to FIG. 1, an embodiment of a system for generating an image in a turbid medium 100 is shown and referenced generally by numeral 10. Turbid medium 100 can be any air or water medium having obscured or opaque optical qualities. For example, turbid water can be found in coastal areas where sediment is stirred up. Turbid water conditions can also be found in polluted water regions. Typical examples of turbid air include fog and smoke-filled regions. It is to be understood that the method of the present invention can be used to generate images in any such turbid medium although the specific hardware elements may be different to accommodate operation in the various turbid mediums.

By way of illustrative example, system 10 will be described for its use in the generation of images in turbid water. System 10 includes the means to (i) illuminate selective portions of a region 102 of turbid medium 100, and (ii) capture images of the illuminated region. In terms of illumination, system 10 includes a light source 12 (e.g., a laser) capable of generating light that will penetrate turbid medium 100. For water, blue light provides the greatest amount of penetration although red light may be preferred for daylight imaging situations and/or because red light experiences less scattering (than blue light) in suspended-particulate mediums. As will be explained further below, light source 12 illuminates some portion of region 102 of medium 100. In general, light source 12 illuminates a number of (discrete or contiguous) locations along a line 14 in region 102.

Light source 12 is mounted on or operatively coupled to a movable platform 16 that changes the position of light source 12 thereby moving line 14. Accordingly, movable platform 16 has a stepper motor 18 coupled thereto for moving movable platform 16 in discrete steps. Stepper motor 18 is controlled by a processor 20.

In terms of capturing images, system 10 has an imager 22 capable of creating/generating an optical image falling within its field-of-view (FOV) that is defined in FIG. 1 between dashed lines 24. For example, imager 22 can be charge coupled device (CCD) camera or any other suitable optical imaging device. Activation of imager 22 for the creation or generation of an optical image can be controlled by processor 20. Each image capture by imager 22 is provided to processor 20 for processing in accordance with the present invention. As would be well understood in the art, processor 20 is assumed to include the necessary memory for storing and processing data. After image processing, processor 20 provides the resulting image data to an output device such as a display 26.

Figure 2:
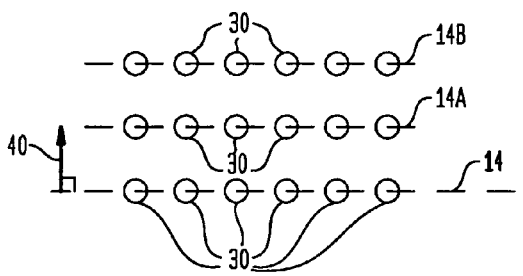
FIG. 2 is a diagrammatic view of a pattern of illuminating light in the form of lines of discrete spots of light where the lines are parallel to one another and the spots in adjacent lines align with one another in a direction that is perpendicular to the lines in accordance with an embodiment of the present invention.

In accordance with the present invention, three spaced apart lines of light (e.g., line 14) are used to create three images for processing in the present invention. Several examples of such spaced apart lines of light are illustrated diagrammatically in FIGS. 2-5. The type of light source 12 needed to generate each illumination embodiment are well known in the art. In FIG. 2, a number of discrete spots of light 30 are arranged along line 14. Such a light pattern could be generated by a dotted line generator as is known in the art. Note that the number of spots used is not a limitation of the present invention. The spacing between adjacent spots 30 on line 14 is typically the same.

After an image is generated of the region that includes spots 30 on line 14, light source 12 is moved to illuminate spots 30 on line 14A which is parallel to line 14. More specifically, line spots 30 on line 14 are moved in a direction that is perpendicular to line 14 as referenced by directional arrow 40. Then, after a second image is generated of the region that includes spots 30 on line 14A, light source 12 is again moved to illuminate spots 30 on line 14B, i.e., spots on line 14A are moved in a direction that is perpendicular to line 14A. With the region illuminated by spots 30 on line 14B, a third image is generated.

Figure 3:
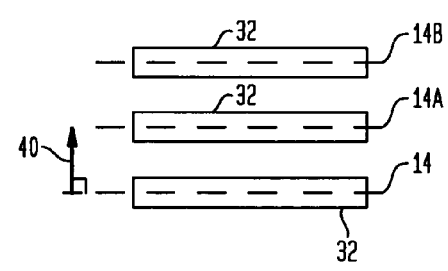
FIG. 3 is a diagrammatic view of another pattern of illuminating light in the form of contiguous lines of light where the lines are parallel to one another and are aligned with one another in accordance with another embodiment of the present invention.

The present invention is not limited to the illumination pattern shown in FIG. 2. For example, as shown in FIG. 3, rather than using discrete spots of the light, the present invention could generate a line of light 32 that is essentially a number of spots of light spaced closely together to form a contiguous line. As in the previous embodiment, three images are generated. The first image is generated when the region is illuminated by line of light 32 along line 14; the second image is generated when the region is illuminated by line of light 32 along line 14A; and the third image is generated when the region is illuminated by line of light 32 along line 14B. Note that use of dotted line illumination (i.e., spots 30) provides the maximum illumination intensity at a location while its small cross-section reduces scattering effects.

Figure 4:
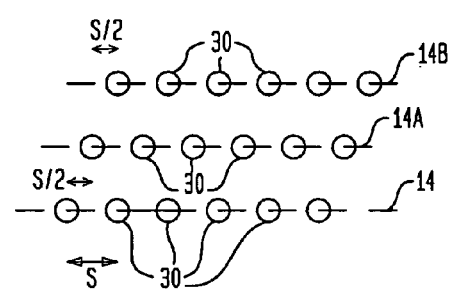
FIG. 4 is a diagrammatic view of another pattern of illuminating light in the form of lines of discrete spots of light where the lines are parallel to one another and the spots in adjacent lines are shifted in accordance with another embodiment of the present invention.

Another illumination example is shown in FIG. 4 where spots 30 along line 14A are still parallel to spots 30 along line 14 as in the FIG. 2 embodiment. However, spots 30 on line 14A are shifted (e.g., by an amount S/2 where S is the spacing between adjacent spots 30) to the right (as shown) or left. In other words, line 14A is moved in an angular direction a relative to line 14. Similarly, spots 30 on line 14B are parallel to spots 30 on line 14A and are shifted (e.g., by an amount S/2). As in the previous illumination embodiments, images of the region are generated when the region is illuminated by along each of lines 14, 14A and 14B.

Figure 5:
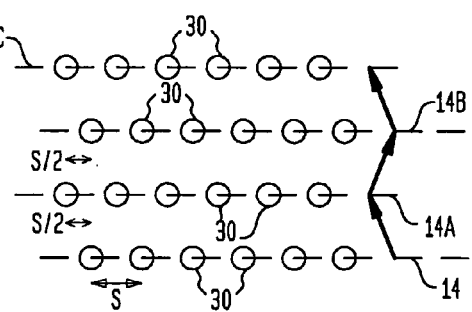
FIG. 5 is a diagrammatic view of another pattern of illuminating light in the form of lines of discrete spots of light where the lines are parallel to one another and the spots in alternate lines are aligned with one another.

Yet another illumination example is shown in FIG. 5 where the shifting of spots 30 (e.g., by an amount equal to S/2) alternates between a shift to the left (as on lines 14A and 14C) and a shift to the right (as on line 14B). As a result, spots 30 on alternate lines are aligned with one another. As in the previous illumination embodiments, images of the region are generated when the region is illuminated along each of three adjacent lines such as lines 14, 14A and 14B.

Figure 6:
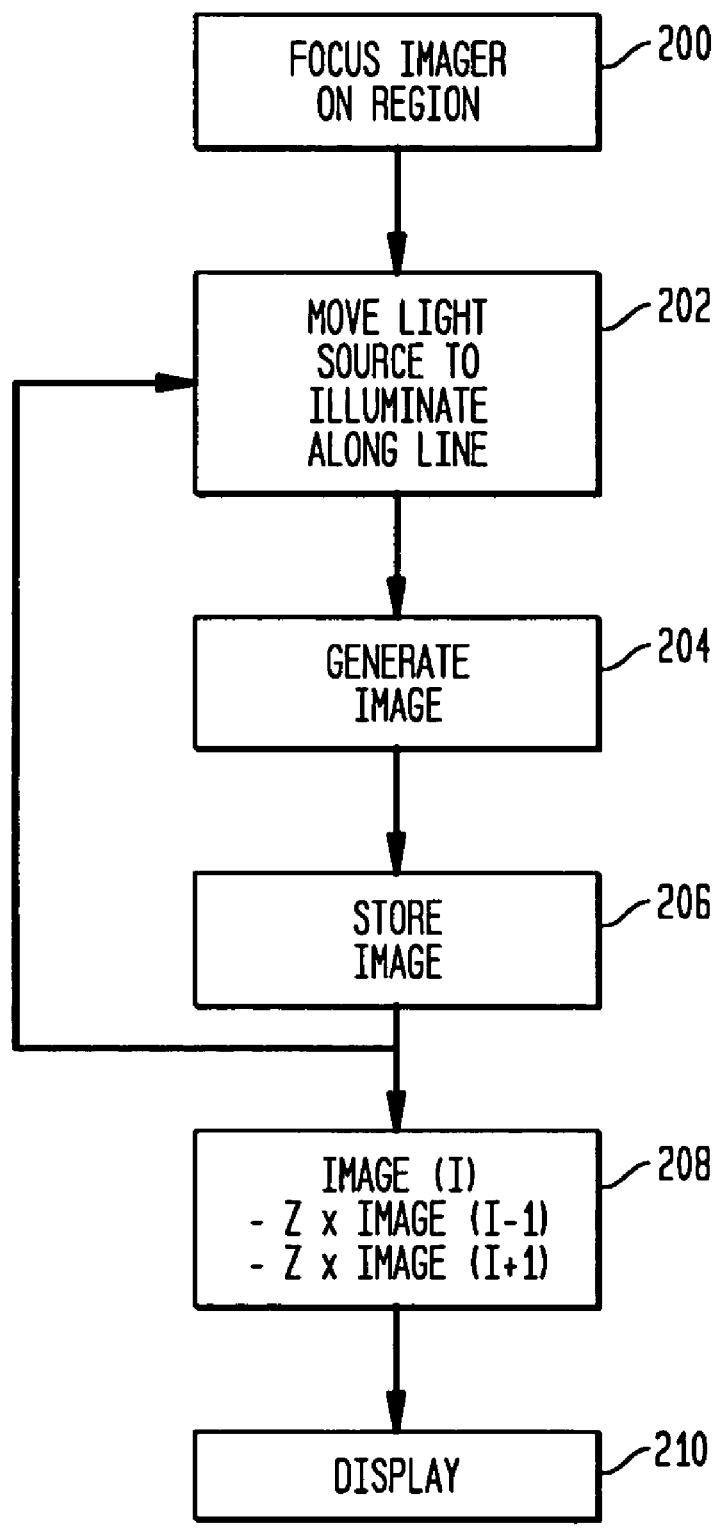
FIG. 6 is a flow chart of the method of processing used to generate an image in accordance with the present invention.

Regardless of the illumination pattern used, the method of the present invention remains the same as will now be described with the flow chart in FIG. 6. At step 200, imager 22 is focused on a region (e.g., region 102) such that the region falls within its FOV 24. Imager 22 remains stationary for the capture/generation of three images with each image being generated while region 102 is illuminated along one of these lines (e.g., lines 14, 14A and 14B). Next at step 202, light source 12 is turned on and moved/positioned to illuminate some of region 102 along line 14. An image of region 102 is generated at step 204 with that image being stored (e.g., at processor 20) at step 206. The previous three steps 202-206 are then repeated so that second and third images are generated while region 102 is illuminated, for example, along lines 14A and 14B, respectively.

Once three images are generated, step 208 sums the three images. As is known in the art of image processing, summing of images involves the pixel-by-pixel summing of pixel amplitudes. In accordance with the present invention, a portion of each of the images (amplitudes) associated with the first and third of three successive images is subtracted from the entirety of the second of three successive images.

As used herein, the second or "I-th" image defines the image generated by a line of illuminating light that is positioned between two other lines of illuminating light. For example, in the illustrated embodiments, the second image is generated when the region is illuminated along line 14A thereby making the first image the "I−1" image and making the third image the "I+1" image. Thus, in general, the summation in step 208 can be written mathematically as

IMAGE($I$)−($Z$×IMAGE($I$−1))−($Z$×IMAGE ($I$+1))

where Z is the portion of the (I−1) and (I+1) image amplitudes that is to be subtracted from the second or I-th image. When attempting to remove scattering and background illumination, Z is preferably 0.5. The resulting line image (e.g., dotted line image in the case where spots 30 are used for illumination) generated by step 208 can be displayed at step 210.

Rather than displaying the line image, the present invention could also be used to generate a three-dimensional (3-D) rendering of the region being imaged and then display such 3-D rendering at step 210. More specifically, it is known from geometry that a straight line projected to a plane remains a straight line. However, if there are any concave or convex features on the plane, the projected line will deform accordingly with the depth of concavity being indicative of the deformation of the projected line. Using standard image processing techniques, the deformation or displacement of the projected line can be measured in pixels and converted to a range measurement. Repeating this analysis across the imaged region (i.e., across the display screen) yields a 3-D profile of the image cross section.

The advantages of the present invention are numerous. Optical imaging in a turbid medium is achieved with a simple and low cost system that does not require expensive time gating or mirror scanning apparatus. The present invention can be used in a variety of turbid mediums simply by adjusting the wavelength of illuminating light. For example, illuminating light in the infrared region might be used when the turbid medium is fog or smoke-filled air. However, it is to be understood that any wavelength of illuminating light can be used provided it penetrates the turbid medium and can be imaged for processing in accordance with the teachings of the present invention.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A method of generating an image of a region in a turbid medium, comprising the steps of:
   illuminating a first plurality of locations along a first line in a turbid medium using beams of light;
   focusing a camera having a field-of-view (FOV) such that said first plurality of locations reside within said FOV wherein a first image is generated;
   illuminating a second plurality of locations along a second line in said turbid medium using beams of light, said second line being displaced relative to said first line;
   focusing said camera such that said second plurality of locations reside within said FOV wherein a second image is generated;
   illuminating a third plurality of locations along a third line in said turbid medium using beams of light, said third line being displaced relative to said first line and said second line with said second line being between said first line and said third line;
   focusing said camera such that said third plurality of locations reside within said FOV wherein a third image is generated; and
   subtracting, in terms of amplitude associated therewith, a portion of each of said first image and said third image from the entirety of said second image, wherein a resulting image is generated.

2. A method according to claim 1 wherein said beams of light are laser beams.

3. A method according to claim 1 wherein said turbid medium is water and said beams of light have wavelength indicative of blue light.

4. A method according to claim 1 wherein said turbid medium is water and said beams of light have wavelength indicative of red light.

5. A method according to claim 1 wherein said turbid medium is one of fog and smoke, and wherein said beams of light have wavelength indicative of infrared light.

6. A method according to claim 1 wherein said portion is approximately 0.5.

7. A method according to claim 1 wherein said steps of focusing include the step of keeping said FOV stationary.

8. A method according to claim 1 wherein said first line, said second line and said third line are parallel to one another.

9. A method according to claim 1 wherein each of said first plurality of locations, said second plurality of locations, and said third plurality of locations is a discrete location.

10. A method according to claim 1 wherein said first plurality of locations are contiguous along said first line, said second plurality of locations are contiguous along said second line, and said third plurality of locations are contiguous along said third line.

11. A method of generating an image of a region in a turbid medium, comprising the steps of:
    focusing a camera's field-of-view (FOV) at a region of a turbid medium;
    illuminating a first plurality of locations along a first line in said region using beams of light;
    activating said camera to generate a first image;
    illuminating a second plurality of locations along a second line in said region using beams of light, said second line being adjacent to said first line;
    activating said camera to generate a second image;
    illuminating a third plurality of locations along a third line in said region using beams of light, said third line being adjacent to said second line wherein said second line is between said first line and said third line;
    activating said camera to generate a third image; and
    subtracting, in terms of amplitude associated therewith, a portion of each of said first image and said third image from the entirety of said second image, wherein a resulting image is generated.

12. A method according to claim 11 wherein said beams of light are laser beams.

13. A method according to claim 11 wherein said turbid medium is water and said beams of light have wavelength indicative of blue light.

14. A method according to claim 11 wherein said turbid medium is water and said beams of light have wavelength indicative of red light.

15. A method according to claim 11 wherein said turbid medium is one of fog and smoke, and wherein said beams of light have wavelength indicative of infrared light.

16. A method according to claim 11 wherein said portion is approximately 0.5.

17. A method according to claim 11 wherein said first line, said second line and said third line are parallel to one another.

18. A method according to claim 11 wherein each of said first plurality of locations, said second plurality of locations, and said third plurality of locations is a discrete location.

19. A method according to claim 11 wherein said first plurality of locations are contiguous along said first line, said second plurality of locations are contiguous along said second line, and said third plurality of locations are contiguous along said third line.

20. A method of generating an image of a region in a turbid medium, comprising the steps of:
    focusing a camera's field-of-view (FOV) at a region of a turbid medium;
    illuminating a first plurality of locations along a first line in said region using beams of light;
    activating said camera to generate a first image;
    illuminating a second plurality of locations along a second line in said region using beams of light, said second line being adjacent and parallel to said first line;

activating said camera to generate a second image;
illuminating a third plurality of locations along a third line in said region using beams of light, said third line being adjacent and parallel to said second line wherein said second line is between said first line and said third line;
activating said camera to generate a third image; and
subtracting, in terms of amplitude associated therewith, one-half of each of said first image and said third image from the entirety of said second image, wherein a resulting image is generated.

* * * * *